United States Patent [19]

Frankel et al.

[11] Patent Number: 4,795,593

[45] Date of Patent: Jan. 3, 1989

[54] 4-AZIDO-4,4-DINITRO-1-BUTANOL AND DERIVATIVES THEREOF

[75] Inventors: Milton B. Frankel, Tarzana; James F. Weber, Moorpark, both of Calif.

[73] Assignee: The United States of America as represented by the Secretary of the Air Force, Washington, D.C.

[21] Appl. No.: 82,775

[22] Filed: Aug. 5, 1987

[51] Int. Cl.$^4$ ...................... C07C 117/00; C06B 25/00
[52] U.S. Cl. ...................................... 260/349; 204/72; 149/88
[58] Field of Search ........................... 260/349; 149/88; 204/72

[56] References Cited

U.S. PATENT DOCUMENTS 3,883,377  5/1975  Wright .................................. 260/349
4,472,311  9/1984  Frankel et al. ....................... 260/349

Primary Examiner—Edward A. Miller
Assistant Examiner—Susan Wolffe
Attorney, Agent, or Firm—Donald J. Singer; Charles E. Bricker

[57] ABSTRACT

There is provided the compound 4-azido-4,4-dinitro-1-butanol (ADNBOH) and a method for making same which comprises reacting trinitromethane and acrolein at a reduced temperature to provide 4,4,4-trinitrobutyraldehyde (TNBAl), reducing the TNBSl to provide 4,4-trinitro-1-butanol (TNBOH) which is further reduced to provide 4,4-dinitro-1-butanol (DNBOH), reacting the DNBOH with acetyl chloride to provide 4,4-dinitro-1-butyl acetate (DNBAc), reacting the DNBAc with an alkali metal azide in an electrolysis cell to provide 4-azido-4,4-dinitro-1-butyl acetate (ADNBAc) and reacting the ADNBAc with a lower alcohol and recovering the 4-azido-4,4-dinitro-1-butanol (ADNBOH).

Also provided are several azidodinitro derivatives of 4-azido-4,4-dinitro-1-butanol and methods for making same.

5 Claims, No Drawings

4-AZIDO-4,4-DINITRO-1-BUTANOL AND DERIVATIVES THEREOF

RIGHTS OF THE GOVERNMENT

The invention described herein may be manufactured and used by or for the Government of the United States for all governmental purposes without the payment of any royalty.

BACKGROUND OF THE INVENTION

This invention relates to energetic organic compounds.

Energetic organic compounds have a long history of use in explosives and propellants. Examples have included polynitroaromatic compounds such as 2,4,6-trinitrotoluene (TNT); cyclic nitramines such as 1,3,5-trinitrazacyclohexane (RDX) and 1,3,5,7,-tetranitrazacyclooctane (HMX); and nitrate esters such as nitrocellulose (NC) and nitroglycerin (NG). Despite some shortcomings in terms of their thermal stability and sensitivity, these materials have seen heavy use during the past century.

More recently, considerable attention has been paid to various polynitro aliphatic compounds. Compounds, such as bis(2,2-dinitropropyl) formal/acetal (BDNPF-A) and bis (2,2,2-fluordinitroethyl) formal (FEFO), have found widespread use as energetic plasticizers in modern explosive and propellant formulations.

Yet another promising class of compounds is the group of azido and azidonitro aliphatic compounds. Despite their well deserved reputation as sensitive materials, organic azides are potentially useful ingredients in energetic formulations because the azido group contributes 80 to 90 kcal/mol, while not detracting from the O/C ratio of the molecule. Incorporating both azido and polynitro functionalities in the same molecule generally has been accomplished by joining individual polynitroalkyl and azidoalkyl moieties via a non-energetic linkage. Examples include azidoalkyl esters of polynitroacids such as 1,3-diazido-2-propyl 4',4',4',-trinitrobutyrate (DAPT) and azide-terminated nitramines such as 1,7-diazido-2,4,6-trinitrazaheptane (DATH) and 1,5-diazido-3-nitrazapentene (DANPE). A more compact combination of these two functionalities would be the use of the azidodinitromethyl group in place of trinitromethyl and fluorodinitromethyl groups, which have been incorporated previously in propellant ingredients.

It is an object of the present invention to provide novel azidodinitro compounds.

It is another object of this invention to provide a method for preparing novel azidodinitro compounds.

Other objects, aspects and advantages of the present invention will be readily apparent to those skilled in the art from a reading of the following detailed disclosure.

SUMMARY OF THE INVENTION

In accordance with the present invention there is provided the compound 4-azido-4,4-dinitro-1-butanol (ADNBOH) and a method for making same which comprises reacting trinitromethane and acrolein at a reduced temperature to provide 4,4,4-trinitrobutyraldehyde (TNBA1), reducing the TNBA1 to provide 4,4,4-trinitro-1-butanol (TNBOH) which is further reduced to provide 4,4-dinitro-1-butanol (DNBOH), reacting the DNBOH with acetyl chloride to provide 4,4-dinitro-1-butyl acetate (DNBAc), reacting the DNBAc with an alkali metal azide in an electrolysis cell to provide 4-azido-4,4-dinitro-1-butyl acetate (ADNBAc) and reacting the ADNBAc with a lower alcohol and recovering the 4-azido-4,4-dinitro-1-butanol (ADNBOH).

Also provided are several azidodinitro derivatives of 4-azido-4,4-dinitro-1-butanol and methods for making same.

DESCRIPTION OF THE PREFERRED EMBODIMENTS 4,4-dinitro-1-butanol (DNBOH) is prepared according to the scheme shown below.

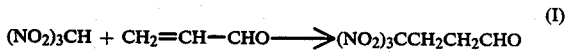  (I)

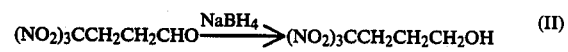  (II)

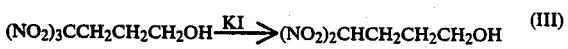  (III)

The addition of trinitromethane to acrolein (Reaction I) is conducted at a temperature of about $-10°$ to $+10°$ C. in aqueous medium. After the addition is complete, the solution may be allowed to warm to room temperature. The organic phase is separated from the aqueous phase and the aqueous phase is extracted with a suitable solvent, such as, for example, methylene chloride. The combined organic layers are washed with water, separated, dried and concentrated to yield the aldehyde.

The reduction of the aldehyde to 4,4,4-trinitro-1-butanol (Reaction II) is conducted at a reduced temperature of about $0°$ to $10°$ C. in alcoholic solution by portionwise addition of the sodium borohydride to the aldehyde solution. After the addition is complete, the solution may be allowed to warm to room temperature. Following removal of the solvent, the remaining material is hydrolyzed with a suitable acid, then extracted with a suitable solvent, such as methylene chloride. The extracts are washed successively with water, a weak basic solution and water, then dried and concentrated to yield the trinitroalcohol.

The conversion of 4,4,4-trinitro-1-butanol to 4,4-dinitro-1-butanol (Reaction III) is conducted by stirring the trinitro alcohol in a suitable alcoholic medium with KI at room temperature or at an elevated temperature. The precipitated potassium salt is filtered, suspended in water, acidified, and then extracted with a suitable organic solvent. The extracts are neutralized, dried and concentrated to yield the dinitro alcohol.

The 4-azido-4,4-dinitro-1-butanol of this invention is prepared according to the following scheme.

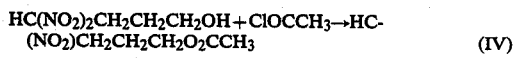  (IV)

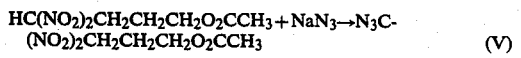  (V)

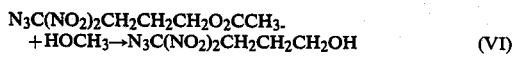  (VI)

The 4,4-dinitro-1-butyl acetate is prepared (Reaction IV) by treating a solution of 4,4-dinitro-1-butanol in a suitable solvent, such as methylene chloride, with acetyl chloride. After complete addition of the acetyl chloride, the resulting mixture is stirred at room temperature for 30 to 120 minutes. The mixture is then quenched with cooled water, separated, dried and concentrated to yield the desired dinitro acetate.

Conversion of the 4,4-dinitro-1-butyl acetate to the corresponding azido dinitro compound (Reaction V) is accomplished by charging the dinitro compound together with aqueous sodium azide and an electrolyte, such as NaOH, to the anode compartment of a divided electrolysis cell, charging aqueous sodium azide to the cathode compartment of the cell and applying a current to the cell. After a suitable reaction period, the reaction is stopped and the anolyte extracted with a suitable solvent, such as methylene chloride. The extract is then washed, dried and concentrated to yield the desired product.

Conversion of the 4-azido-4,4-dinitro-1-butyl acetate to the corresponding alcohol (Reaction VI) is accomplished by treating the acetate with acidified lower aliphatic alcohol, such as methanol, at room temperature.

The 4-azido-4,4-dinitro-1-butanol may be converted to a variety of derivatives according to the following reaction schemes, wherein R is an alkyl group having 1 to 5 carbon atoms, and X is —Cl, —Br or —F:

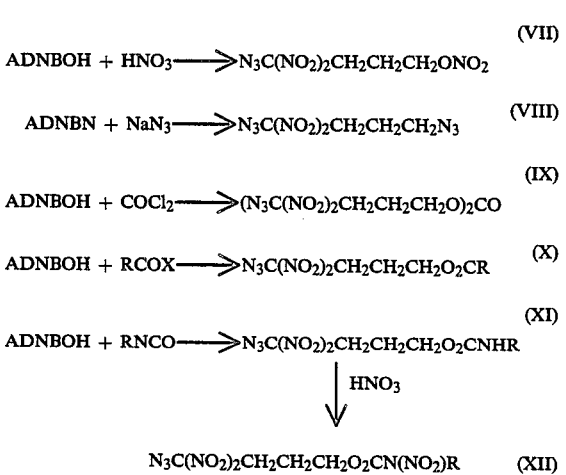

Conversion of ADNBOH to 4-azido-4,4-dinitro-1-butyl nitrate (ADNBN) (Reaction VII) is accomplished by reacting the ADNBOH with concentrated nitric acid in a suitable solvent, such as methylene chloride, at a reduced temperature of about 0°–10° C.

Conversion of the ADNBN to 1,4-diazido-4,4-dinitro butane (Reaction VIII) is accomplished by reacting ADNBN with an alkali metal azide in a suitable organic solvent, such as dimethyl sulfoxide or dimethyl formamide, at a temperature of about 60°–90° C.

Conversion of ADNBOH to 4-azido-4,4-dinitro-butyl carbonate (Reaction IX) may be accomplished by treating the ADNBOH with phosgene at a temperature of about 0°–10° C.

The ADNBOH may be esterified as shown in reaction X by reacting ADNBOH with an alkyl carboxylic acid halide, RCOX, wherein R and X are as described previously, by addition of the acid halide to the ADNBOH in a suitable solvent such as methylene chloride. After completion of the reaction the product is quenched with cooled water, and purified by appropriate means.

Urethane derivations of ADNBOH are prepared (Reaction XI) by addition of the alkyl isocyenate to ADNBOH in a suitable solvent and warming to 60°–90° for two hours. Cooling and recrystallization yields the pure product.

Nitration of the urethane (Reaction XII) by nitric acid gives the corresponding N-nitro urethane.

The following examples illustrate the invention.

EXAMPLE I

4,4,4-Trinitrobutyraldehyde

A 12 L three-necked, round-bottom flask with a thermometer, mechanical stirrer, and 1000 mL addition funnel was charged with 6377 g of an 11% aqueous nitroform solution (701.5 g; 4.675 mol) and cooled in a dry-ice bath at 9° C. A solution of acrolein (274.1 g, 4.90 mol) in 2000 mL of water was added at a rate that maintained the temperature at 0° C. The dry-ice bath was removed and the stirred solution allowed to warm to room temperature overnight. The two phases were separated and the aqueous layer was extracted with $CH_2Cl_2$ (2×2000 mL). The combined organic layers were washed with water (2×2000 mL). The product was dried ($MgSO_4$) and concentrated to give 878 g (91%) of the aldehyde as a yellow oil; $n_D=1.4731$ (26° C.). The infrared spectrum showed band at 1725 cm$^{-1}$ (C=O), 1590, 1300, and 800 cm$^{-1}$ ($NO_2$).

EXAMPLE II

4,4,4-trinitro-1-Butanol

Crude 4,4,4-trinitrobutaldehyde (878 g, 4.24 mol) was dissolved in methanol (1000 mL) and cooled in an ice bath while $NaBH_4$ (130.7 g 3.44 mol) was added portion-wise. The mixture was stirred at room temperature overnight under a nitrogen purge which removed much of the solvent. The thick suspension was hydrolyzed with 6N HCl (approx. 4 L) and the product extracted with $CH_2Cl_2$ (3×100 mL). The extracts were washed with water (1000 mL), saturated $NaHCO_3$ (2×1000 mL), and water (1000 mL). The product solution was dried ($MgSO_4$) and concentrated to yield 554 g (63%) of a yellow oil, n=1.4735 (19° C.). The infrared spectrum showed peaks at 3619, 3370, 2950, 2890, 1595, 1305, 1058 and 801 cm$^{-1}$.

EXAMPLE III

4,4-Dinitro-1-Butanol

This alcohol was prepared by stirring TNBOH (554 g, 2.65 mol) in methanol (6 L) with KI (1426 g, 8.6 mol) for 6 days at room temperature. The precipitated potassium salt was filtered, suspended in water (4 L), acidified with concentrated HCl (250 mL), and extracted into $CH_2Cl_2$ (6×500 mL). The extracts were washed with 10% $NaHSO_3$ (1000 mL). The solution was dried ($MgSO_4$ and concentrated to give the product (220 g, 51%) as a yellow oil. The infrared spectrum had peaks at 3450, 2950, 1575, 1340, and 1070 cm$^{-1}$.

EXAMPLE IV

4,4-Dinitro-1-Butyl Acetate

This ester was synthesized by treating a solution of DNBOH (39.2 g, 0.24 mols) in $CH_2Cl_2$ (100 mL) with acetyl chloride (22 mL, 24 g, 0.31 mol). After 90 minutes at room temperature, the reaction was quenched with ice water. Separation, drying ($MgSO_4$), and concentration of the organic phase gave the product (42.7 g, 87%) as a light yellow oil; $n_D=1.4574$ (24° C.). The infrared spectrum of DNBAc had beaks at 2960, 1745, 1575, 1245, and 1060 cm$^{-1}$. Elemental analyses—Calculated for $C_6H_{10}N_2O_6$: C, 34.95; H, 4.85; N, 13.59; Found: C, 35.17; H, 4.83; N, 12.95.

EXAMPLE V

4-Azido-4,4-Dinitro-1-Butyl Acetate

A divided electrochemical H-cell was charged with 4,4-dinitrobutyl acetate (10.2 g), 30% aqueous $NaN_3$ (25 mL) and 12N NaOH (4 mL) in the anode compartment and 30% $NaN_3$ (35 mL) in the cathode compartment. This solution was electrolyzed at 650 mA using a platimum foil anode (6.5 cm$^2$) and a stainless steel cathode. After 5.25 h the reaction was stopped, and the anolyte was extracted with $CH_2Cl_2$ (3×25 mL). Brine-washing, drying, and concentrating the extracts yielded a product which displayed a weak hydroxyl absorption in the infrared spectrum. The product was reacetylated by stirring with acetyl chloride (1 mL) in $CH_2Cl_2$ (30 mL) for 2 h. This reaction was quenched in ice water, dried, and concentrated. The crude yellow oil was purified by column chromatography on silica gel eluting with 10% ethyl acetate in hexanes. The purified product was a clear light yellow oil which was greater than 95% pure by HPLC: $n_D = 1.4649$ (25° C.); IR: 2165, 1735, and 1590 cm$^{-1}$; NMR (CDCl$_3$): 4.07 (q, 2H), 2.58 (m, 2H), 2.07 (s, 3H), 1.73 (m, 2H). Elemental analyses calculated for $C_6H_9N_5O_6$: C, 29.15; H, 3.64; N, 28.34. Found: C, 29.59; H, 3.90; N, 27.89.

EXAMPLE VI

4-Azido-4,4-Dinitro-1-Butanol

A solution consisting of 2.3 g of ADNBAc in a 3% HCl/MeOH solution (40 mL) was stirred at room temperature for 3.5 h. Filtering and concentrating the reaction mixture gave a light yellow oil which was dissolved in 30 mL of methylene chloride and filtered through a silica gel pad. Concentration of the filtrate gave the alcohol (19 g, 97%) in good purity: $n_D = 1.4833$ (21° C.); IR: 3380, 2175 and 1580 cm$^{-1}$; NMR (CDCl$_3$, FIG. 25): 3.65 (t, 2H), 2.95 (s, 1H), 2.60 (m, 2H), 1.62 (m, 2H). Elemental analyses Calculated for $C_4H_7N_5O_5$: C, 23.41; H, 3.41; N, 34.15. Found: C, 23.45; H, 3.39; N, 32.83.

EXAMPLE VII

4-azido-4,4-dinitro-1-butyl nitrate

A solution of 4-azido-4,4-dinitro-1-butanol (3.1 g) in methylene chloride (10 mL) was added dropwise with stirring to a solution of anhydrous nitric acid in methylene chloride (25 mL) with cooling by an ice bath. Upon completion of the addition, the reaction was allowed to warm to room temperature for 1 h. The reaction mixture was then poured on ice and washed with water, bicarbonate solution, and brine, dried, and concentrated to give 3.1 g (82%) of the nitrate ester: $n_D = 1.4052$ (24° C.); IR: 2160, 1635 and 1580 cm$^{-1}$; NMR (CDCl$_3$): 4.52 (t,2H), 2.63 (m, 2H), 1.83 (M, 2H). Elemental analyses—Calculated for $C_4H_6N_6O_7$: C, 19.20; H, 2.40; N, 33.60. Found: C, 1.955; H, 2.49; N, 31.65.

Various modification may be made without departing from the spirit of the invention or the scope of the appended claims.

We claim:

1. 4-azido-4,4-dinitro-1-butanol.
2. A method for preparing 4-azido-4,4-dinitro-1-butanol which comprises the steps of reacting 4,4-dinitro-1-butanol with acetyl chloride to yeild 4,4-dinitro-1-butyl acetate, reacting said acetate with an alkali metal azide in an electrolysis cell to yield 4-azido-4,4-dinitro-1-butyl acetate, and reacting said 4-azido-4,4-dinitro-1-butyl acetate with a lower alkyl alcohol.
3. 4-azido-4,4-dinitro-1-butyl nitrate.
4. 1,4-diazido-4,4-dinitro butane.
5. 4-azido-4,4-dinitro butyl carbonate.

* * * * *